United States Patent [19]
Eyer et al.

[11] Patent Number: 5,756,756
[45] Date of Patent: May 26, 1998

[54] ASYMMETRIC HYDROGENATION OF DIHYROFUROIMIDAZOLE DERIVATIVES

[75] Inventors: Martin Eyer, Brig-Glis; Rudolf Fuchs, Sion; John McGarrity, Visp, all of Switzerland

[73] Assignee: Lonza, Ltd., Gampel/Valais, Switzerland

[21] Appl. No.: 898,119

[22] Filed: Jul. 22, 1997

Related U.S. Application Data

[63] Continuation of Ser. No. 536,680, Sep. 29, 1995, abandoned, which is a continuation of Ser. No. 238,481, May 5, 1994, abandoned, which is a division of Ser. No. 167,362, Dec. 16, 1993, abandoned.

[30] Foreign Application Priority Data

Dec. 18, 1992 [CH] Switzerland ............... 3873/92
Feb. 18, 1993 [CH] Switzerland ............... 498/93

[51] Int. Cl.$^6$ ........................... C07D 491/48
[52] U.S. Cl. ........................... 548/303.1
[58] Field of Search ........................... 548/303.1

[56] References Cited

U.S. PATENT DOCUMENTS

| | | | |
|---|---|---|---|
| 4,851,540 | 7/1989 | McGarrity | 548/110 |
| 4,876,350 | 10/1989 | McGarrity | 548/110 |
| 4,937,351 | 6/1990 | Poetsch | 548/303.7 |
| 5,162,540 | 11/1992 | McGarrity | 658/303 |
| 5,235,065 | 8/1993 | Schuarz | 548/303.7 |

FOREIGN PATENT DOCUMENTS

| | | |
|---|---|---|
| 0 270 076 | 6/1988 | European Pat. Off. . |
| 0 273 270 | 7/1988 | European Pat. Off. . |
| 2058248 | 6/1971 | Germany . |
| 45-31669 | of 1970 | Japan . |
| 53-27279 | of 1978 | Japan . |

OTHER PUBLICATIONS

M. Fiorini et al., J. Mol. Catal., 5, (1979), 303 and M. Fiorini et al., J. Mol. Catal., 7, (1980), 411.
J. Chatt et al., J. Chem. Soc., (1957), 4735.
G. Giordano et al., Inorg. Synth., 19, (1979), 218.
McOmie, Protective Groups in Organic Chemistry p. 63, (1973).

Primary Examiner—Robert Gerstl
Attorney, Agent, or Firm—Fisher, Christen & Sabol

[57] ABSTRACT

A process for the asymmetric hydrogenation of the furoimidazole derivatives of the general formula:

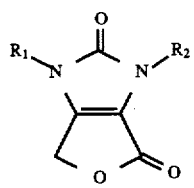

I wherein $R_1$ is a protective group, which is cleavable in a known way, and $R_2$ is hydrogen or a protective group, which is cleavable in a known way, with hydrogen in the presence of a homogeneous catalyst to the corresponding diastereomeric tetrahydrofuroimidazole derivatives of the general formula:

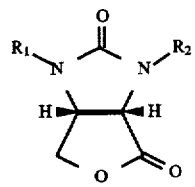

II

The tetrahydrofuroimidazole derivatives of the general formula II are intermediate products for the production of vitamin (+) biotin.

1 Claim, No Drawings

5,756,756

ASYMMETRIC HYDROGENATION OF DIHYROFUROIMIDAZOLE DERIVATIVES

This application is a Continuation of prior U.S. application Ser. No. 08/536,680 filing date Sep. 29, 1995 which is a continuation of application Ser. No. 08/238,481 filing date May 5, 1994 which is a division of application Ser. No. 08/167,362 filing date Dec. 16, 1993 all now abandoned.

BACKGROUND OF THE INVENTION

1. Field of the Invention

The invention relates to a new process for the asymmetric hydrogenation of the dihydrofuroimidazole derivatives of the general formula:

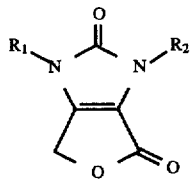

in which $R_1$ means a protective group which is cleavable in a known way and $R_2$ stands for hydrogen or a protective group which is cleavable in a known way, with hydrogen in the presence of a homogeneous catalyst to the corresponding diastereomeric tetrahydrofuroimidazole derivatives of general formula:

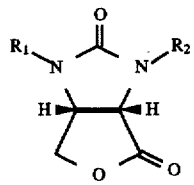

in which $R_1$ and $R_2$ have the above-mentioned meanings.

2. Background Art

Most known (+) biotin syntheses pursue the aim of dividing suitable precursors by, for the most part, very costly methods of racemate resolution with, for the most part, very expensive cleaving agents and further pursue the (+)-biotin synthesis with the resulting diastereomers (see, e.g., German Patent No. 2,058,248). Then, according to European Published Patent Application No. 273,270, the introduction of the relevant optically active centers, meaning the 3aS and 6aR positions of the biotin ring structure, was achieved for the first time by an asymmetric hydrogenation of the corresponding dihydrofuroimidazole derivatives with a typical hydrogenation catalyst, such as, rhodium on aluminum oxide. This process was not completely satisfactory because of the attainable yield of the desired diastereomer.

BROAD DESCRIPTION OF THE INVENTION

The main objective of the invention is to provide an improved asymmetric hydrogenation process with which the mentioned key step of the biotin synthesis can be performed with very good diastereo-selectivity with good yield of the tetrahydrofuroimidazole.

Other objectives and advantages of the invention are set out herein or are obvious herefrom to one skilled in the art.

The objectives and advantages of the invention are achieved by the process and compounds of the invention.

The invention involves a process for the asymmetric hydrogenation of the dihydrofuroimidazole derivatives of general formula:

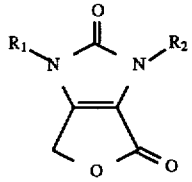

wherein $R_1$ is a protective group which is cleavable in a known way and $R_2$ is a hydrogen or a protective group which is cleavable in a known way with hydrogen in the presence of a homogeneous catalyst to the corresponding diastereomeric tetrahydrofuroimidazole derivatives of the general formula:

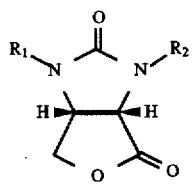

wherein $R_1$ and $R_2$ have the above-mentioned meanings. The homogeneous catalysts that are used can be obtained by reaction of a Rh complex with a chiral phoshine ligand from the group consisting of:

(a) 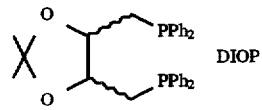 DIOP   III and (b) 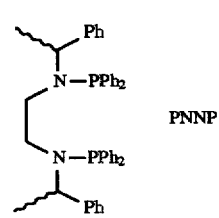 PNNP   IV wherein Ph is a phenyl group.

The tetrahydrofuroimidazoles of the general formula II are important intermediate products in the synthesis of (+)-biotin, a vitamin essential for humans, that is also designated vitamin H. Moreover, (+)-biotin is used as a pharmaceutical agent for the treatment of dermatosis or as a feed additive with growth increasing effect for domestic animals.

Preferably the protective groups, which are cleavable in a known way, of $R_1$ are phenyl-$(C_1-C_6)$-alkyl groups, benzyl groups, and naphthyl-$(C_1-C_6)$-alkyl groups, and the aromatic nuclei of the respective groups are optionally substituted with one or more substituents from the listing composed of $(C_1-C_6)$-alkyl, $(C_1-C_6)$-alkoxy, hydroxy, halo, amino, $(C_1-C_6)$-alkylamino and $(C_1-C_6)$-dialkylamino. Preferably the protective groups, which are cleavable in a known way, of $R_2$ are $(C_1-C_6)$-alkanoyl groups, $(C_1-C_6)$-alkoxy-$(C_1-C_6)$-alkyl groups, $(C_1-C_6)$-alkoxycarbonyl groups, aroyl groups and benzyl, and the aromatic nuclei of the respective groups are optionally substituted with one or more substituents from the listing composed of $(C_1-C_6)$-alkyl, $(C_1-C_6)$-alkoxy, hydroxy, halo, amino, $(C_1-C_6)$-alkylamino and $(C_1-C_6)$-dialkylamino. Preferably the (−)-DIOP ligand or the (S,S)-PNNP ligand is used as the chiral phosphine legand in the catalyst. Preferably Rh complexes of the general formula:

$$Rh(O): [Rh(L)A]_2 \qquad V$$

or $$Rh(+): [Rh(L)_2]B^- \qquad VI$$

wherein L stands for two $C_2$–$C_{12}$ olefins or a $C_5$–$C_{12}$-diene, A represents a halogen and $B^-$ is an anion of an oxygen acid or complex acid, are used as the catalyst. Preferably the reaction takes place at a hydrogen pressure of 1 to 200 bars and a reaction temperature of 25° to 150° C. Preferably the amount of catalyst, expressed as a ratio of dihydrofuroimidazole to homogeneous catalyst, ranges between 100:1 and 5000:1. Preferably aprotic solvents are used, and preferably the aprotic solvent is toluene.

The invention also involves (3aS–6aR)-tetrahydrofuroimidazole derivatives of general formula II wherein $R_1$ is a phenyl($C_1$–$C_6$)-alkyl group, whose aromatic nucleus is substituted with one or more substituents from the listing composed of ($C_1$–$C_6$)-alkyl, ($C_1$–$C_6$)-alkoxy, hydroxy, halo, amino, ($C_1$–$C_6$)-alkylamino, and ($C_1$–$C_6$)-dialkylamino, or $R_1$ is a naphthyl-($C_1$–$C_6$)-alkyl group, whose aromatic nuclei are optionally substituted with one or more of the above-mentioned substituents. Preferably $R_1$ in the (3aS–6aR)-tetrahydrofuroimidazole derivatives is an (R) or (S)-1-phenylethyl group or an (R) or (S)-1-naphthylethyl group.

DETAILED DESCRIPTION OF THE INVENTION

The dihydrofuroimidazoles of the general formula I can be produced according to the disclosure and instructions of European Published Patent Application Nos. 273,270 and 270,076, and U.S. Pat. Nos. 5,162,540, 4,876,350 and 4,851,540.

Suitably the following groups are used as the protective groups, which are cleavable in a known way, of $R_1$: A phenyl-($C_1$–$C_6$)-alkyl group, a benzyl group or a naphthyl-($C_1$–$C_6$)-alkyl group; their aromatic nuclei can be optionally substituted with one or more substituents from the listing composed of ($C_1$–$C_6$)-alkyl, ($C_1$–$C_6$)-alkoxy, hydroxy, halo, amino, ($C_1$–$C_6$)-alkylamino, ($C_1$–$C_6$)-dialkylamino. Halo herein can be chloro, bromo, iodo or fluoro. The phenyl-($C_1$–$C_6$)-alkyl group or the naphthyl-($C_1$–$C_6$)-alkyl group can have a chiral center. $R_1$ preferably is an (R) or (S)-1-phenylethyl group, a benzyl group or an (R) or (S)-1-naphthylethyl group, and the aromatic nuclei of the preferred groups can be substituted with the above-mentioned substituents.

$R_2$ suitably is a hydrogen or a protective group, which is cleavable in a known way, selected from the group composed of the ($C_1$–$C_6$)-alkanoyl, benzyl, ($C_1$–$C_6$)-alkoxy-($C_1$–$C_6$)-alkyl, ($C_1$–$C_6$)-alkoxycarbonyl and aroyl, such as, benzoyl; the aromatic nucleus of the benzyl group or the aroyl groups can be substituted corresponding to the aromatic nucleus of $R_1$. $R_2$ preferably is acetyl, benzyl, ($C_1$–$C_2$)-alkoxy-($C_1$–$C_2$)-alkyl, ($C_1$–$C_2$)-alkoxycarbonyl or benzoyl.

It was found that surprisingly homogeneous catalysts that can be obtained by reaction of an Rh complex with a chiral phosphine ligand from the series of:

(a) DIOP  III (b) PNNP  IV wherein Ph is a phenyl group, in comparison to the process of the prior art, provide a greatly increased diastereo selectivity with, at the same time, good yield in the invention process.

The (–)-DIOP ligand is the preferred DIOP ligand. The (S,S)-PNNP ligand is the preferred PNNP ligand. Both DIOP and PNNP ligands are known in the literature, for example:

T. P. Dana et al., J. Chem. Soc. Chem. Commun., (1971), 481. (DIOP).

M. Fiorini et al., J. Mol. Catal., 5, (1979), 303 and J. Mol. Catal., 7, (1980), 411. (PNNP).

As Rh complexes those of the general formula:

$$Rh(O): [Rh(L)A]_2 \qquad V$$

or $$Rh(+): [Rh(L)_2]B^- \qquad VI$$

wherein L stands for two $C_2$–$C_{12}$ olefins (one double bond) or a $C_5$–$C_{12}$-diene, A is a halogen and $B^-$ means an anion of an oxygen acid or complex acid, are used. L, when it means olefin, preferably contains 2 to 6 C atoms and when it means diene, preferably contains 5 to 8 C atoms. In this way the diene can be open-chained, monocyclic or bicyclic. Examples of the olefins are ethylene, propene and 1-butene. Examples of the dienes are 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene, and norbornadiene. Preferably L is two ethylenes, 1,5-hexadiene, 1,5-cyclooctadiene or norbornadiene. A preferably is chlorine or bromine. Examples of $B^-$ are $ClO_4^-$, $FSO_3^-$, $CH_3SO_3^-$, $CF_3SO_3^-$, $BF_4^-$, $PF_6^-$, $SbCl_6^-$, $AsF_6^-$ and $SbF_6^-$. Preferably $B^-$ is $BF_4^-$, $ClO_4^-$, $PF_6^-$, $CF_3SO_3^-$ or $SbF_6^-$.

The production of these Rh complexes is known and is disclosed, for example, in J. Chatt et al., J. Chem. Soc., (1957), 4735, and G. Giordano et al., Inorg. Synth., 19, (1979), 218.

The production of the active homogeneous catalyst suitably takes place in situ, i.e., in the context of the hydrogenation of the respective dihydrofuroimidazole of the general formula I. Suitably the procedure is that first the homogeneous catalyst components, i.e., the Rh complex and the corresponding phosphine ligand, are introduced together with the corresponding dihydrofuroimidazole derivative in a suitable inert solvent. With attention being paid to appropriate precautions, the reaction is advantageously performed in an oxygen-free inert gas atmosphere.

As the suitable inert solvents that can be used by themselves or in mixture, aprotic solvents, such as, aliphatic and aromatic hydrocarbons, and halogenated hydrocarbons, are suitable. Suitable representatives of the aromatic hydrocarbons solvents are, e.g., benzene, toluene and xylene, the aliphatic hydrocarbons are, e.g., hexane and pentane, and the halogenated hydrocarbons are, e.g., methylene chloride or chloroform. An especially suitable solvent is toluene. It can possibly be of advantage to use a mixture of one of the mentioned aprotic solvents with a protic solvent such as, the aliphatic alcohols. Methanol is an especially suitable aliphatic alcohol solvent.

The amount of the solvent is suitably selected so that a substrate concentration of 2 to 30 percent is obtained. Preferably the process is carried out at a substrate concentration of about 10 percent. The amount of the catalyst, expressed as a ratio of the substrate (dihydrofuroimidazole) to the catalyst, suitably ranges between 100:1 and 5000:1, preferably in the amount of about 500:1. The reaction takes place advantageously at a hydrogen pressure between 1 and 200 bars, preferably 1 to 20 bars and at a reaction temperature between 25° and 150° C., preferably between 40° C. and 90° C.

After the hydrogenation, the desired diastereomeric (3aS–6aR)-tetrahydrofuroimidazole of general formula II can be isolated in a way known to one skilled in the art. Possible parts of the unwanted (3aR–6aS)-tetrahydrofuroimidazole can be removed by recrystallization with a suitable solvent, such as, methylisobutyl ketone, ethyl acetate or toluene.

The resulting tetrahydrofuroimidazoles then can be further reacted to the (+) biotin, for example, according to Europen Published Patent Application No. 273,270 and U.S. Pat. Nos. 5,162,540 and 4,876,350. In the last step in the production process of (+)-biotin disclosed in these patents, the protective groups can be cleaved off (which illustrates what is meant herein by protective groups which are cleavable in a known way. For example, the protective groups can be cleaved off by treatment with methanesulfonic acid with heating according to teachings of Japanese Patent Publication Nos. 31669/1970 and 27279/1978.

The invention includes the tetrahydrofuroimidazole derivatives of the general formula II wherein $R_1$ is a phenyl $(C_1-C_6)$-alkyl group, whose aromatic nucleus is substituted with one or more substituents from the listing composed of $(C_1-C_6)$-alkyl, $(C_1-C_6)$-alkoxy, hydroxy, a halogen, amino, $(C_1-C_6)$-alkylamino, and $(C_1-C_6)$-dialkylamino, or wherein $R_1$ is naphthyl-$(C_1-C_6)$-alkyl that is optionally substituted with one or more of the afore-mentioned substituents, and $R_2$ is hydrogen or a protective group which is cleavable in a known way (for example, $(C_1-C_6)$-alkanoyls, $(C_1-C_6)$ alkoxy-$(C_1-C_6)$-alkyls, $(C_1-C_6)$-alkoxycarbonyls, aroyls and benzyl; and the aromatic nuclei of the respective groups are optionally substituted with one or more substituents of the following: $(C_1-C_6)$-alkyl, $(C_1-C_6)$-alkoxy, hydroxy, halo, amino, $(C_1-C_6)$-alkylamino and $(C_1-C_6)$-dialkylamino). These compounds are not known in the literature. Preferably, in these new compounds, $R_1$ is an (R) or (S)-1-phenylethyl group whose aromatic nucleus is substituted with one or more of the above-mentioned substituents, or is an (R) or (S)-1-naphthylethyl group.

EXAMPLE 1

Production of (3aS, 6aR)-tetrahydro-1-[(R)-1-phenylethyl]furo[3,4-d]imidazole-2,4-dione Under exclusion of oxygen, an autoclave was provided with 3.4 g of 3,6-dihydro-1-[(R)-1-phenylethyl]-1H-furo[3,4-d]imidazole-2,4-dione, 13.7 mg of chloro rhodium (1,5-cyclooctadiene)-dimer and 27.9 mg of (−)-DIOP. After flushing with argon, 75 ml of oxygen-free toluene was added. The reaction was allowed to proceed for 4 hours at an $H_2$ pressure of 14 bars and a temperature of 90° C. Afterwards, the HPLC analysis showed a 98 percent conversion and a diastereo selectivity (de) of 54 percent relative to the desired RRS isomer. The autoclave pressure was released and it was flushed with nitrogen. The reaction mixture was filtered. The crude product was recrystallized in ethyl acetate. 2.25 g (65 percent) of the pure title product was obtained. The product had a melting point of 156° to 158° C. Other data for the product was:

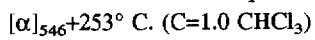

EXAMPLE 2

Production of (3aS,6aR)-tetrahydro-1-[(R)-1-phenylethyl]furo[3,4-d]imidazole-2,4-dione Under exclusion of oxygen an autoclave was provided with 3.4 g of 3,6-dihydro-1-[(R)-1-phenylethyl]-1H-furo[3,4-d]imidazole-2,4-dione, 13.7 mg of chloro rhodium (1,5-cyclooctadiene)-dimer and 27.9 mg of (S,S)-PNNP. After flushing with argon, 75 ml of oxygen-free toluene was added. The reaction was allowed to proceed for 4 hours at an $H_2$ pressure of 14 bars and a temperature of 90° C. Afterwards, the HPLC analysis showed a 98 percent conversion and a diastereo selectivity (de) of 54 percent relative to the desired RRS isomer. The autoclave pressure was released and it was flushed with nitrogen. The reaction mixture was filtered. The crude product was recrystallized in ethyl acetate. 2.3 g (67 percent) of the pure title product was obtained. The product had a melting point of 157° to 158° C. Other data for the product was:

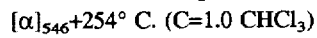

EXAMPLE 3

Production of (3aS,6aR)-3-benzyltetrahydro-1-[(R)-1-phenylethyl]furo[3,4-d]imidazole-2,4-dione The reaction took place basically according to Example 1. The molar ratio of feedstock/catalyst was 500/1. The reaction was allowed to proceed for 60 hours at 70° C. and an $H_2$ pressure of 50 bars. A de of 50 percent was obtained. Other data for the product was:

$^1$H-NMR (CDCl$_3$, 400 MHz) δ in ppm 1.57 (d, 3H, J=7.1 Hz);

5.34 (q, 1H)

5.03 (d, 1H, J=14.8 Hz);

4.32 (d, 1H);

3.89 (d, 1H, J=9.2 Hz);

4.35 (m, 1H, J=5.7 Hz);

3.82 (dd, 1H, J=2.7 Hz);

3.38 (df, 1H, J=10.4 Hz);

7.3–7.4 (m, 10H).

EXAMPLE 4

Production of (3aS,6aR)-tetrahydro-1-(2-methoxybenzyl)furo[3,4-d]imidazole-2,4-dione The reaction took place basically according to Example 1. The molar ratio of feedstock/catalyst was 250/1. The reaction was allowed to proceed for 18 hours at 70° C. and an $H_2$ pressure of 75 bars. A de of 60 percent was obtained. Other data for the product was:

$^1$H-NMR (CDCl$_3$, 400 MHz) δ in ppm
3.84 (s, 3H);
4.12 (d, 1H, J=7.7 Hz);
4.25–4.35 (m, 3H);
4.45 (d, 1H, J=10.1 Hz);
4.64 (d, 1H, FJ=14.8 Hz);
5.63 (s, 1H);
6.89 (d, 1H, J=8.1 Hz);
6.95 (t, 1H, J=7.5 Hz);
7.27–7.32 (m, 2H).

EXAMPLE 5

Production of (3aS,6aR)-tetrahydro-1-[(R)-1-(2-methoxyphenyl)ethyl]furo[3,4-d]imidazole-2,4-dione The reaction took place basically according to Example 1. The molar ratio of feedstock/catalyst was 130/1. The reaction was allowed to proceed for 18 hours at 70° C. and an H$_2$ pressure of 85 bars. A de of 50 percent was obtained. Other data for the product was:

$^1$H-NMR (DMSO-d$_6$, 400 MHz) δ in ppm
1.59 (d, 3H, J=7.5 Hz);
3.59 (d, 1H, J=11 Hz);
3.85 (s, 3H);
3.95 (dd, 1H, J=11+5 Hz);
4.17 (d, 1H, J=9 Hz);
4.53 (m, 1H);
5.42 (s, 1H);
5.43 (q, 1H);
6.91 (d, 1H, J=8 Hz);
6.98 (t, 1H, J=7 Hz);
7.25–7.40 (m, 1H).

EXAMPLE 6

Production of (3aS,6aR)-3-acetyltetrahydro-1-[(R)-1-phenylethyl]furo[3,4-d]imidazole-2,4-dione The reaction took place basically according to Example 1. The molar ratio of feedstock/catalyst was 500/1. The reaction was allowed to proceed for 60 hours at 70° C. and an H$_2$ pressure of 30 bars. A de of 33 percent was obtained. Other data for the product was:

$^1$H-NMR (CDCl$_3$, 400 MHz) δ in ppm
1.65 (d, 3H, J=6.5 Hz);
2.55 (s, 3H);
3.57 (d, 1H, J=10 Hz);
4.08 (dd, 1H, J=4.0 Hz);
4.58 (dd, 1H, J=9 Hz);
5.27 (d, 1H, J=9 Hz);
5.30 (m, 1H).

EXAMPLE 7

Production of (3aS,6aR)-1-benzyltetrahydrofuro[3,4-d]imidazole-2,4-dione

The reaction took place basically according to Example 1. The molar ratio of feedstock/catalyst was 500/1. The reaction was allowed to proceed for 48 hours at 70° C. and an H$_2$ pressure of 30 bars. A de of 50 percent was obtained. Other data for the product was:

$^1$H-NMR (CDCl$_3$, 400 MHz) δ in ppm
4.19 (d, 1H, J=8.0 Hz);
4.25–4.32 (m, 4H);
4.68 (d, 1H, J=15.2 Hz);
5.19 (s, 1H);
7.24–7.39 (m, 5H).

EXAMPLE 8

Production of (3aS,6aR)-tetrahydro-1-[(R)-1-naphthalin-1-ylethyl]furo[3,4-d]imidazole-2,4-dione The reaction took place basically according to Example 1. The molar ratio of feedstock/catalyst was 125/1. The reaction was allowed to proceed for 18 hours at 70° C. and an H$_2$ pressure of 75 bars. A de of 72 percent was obtained. Other data for the product was:

$^1$H-NMR (CDCl$_3$, 400 MHz) δ in ppm
1.70 (d, 3H, J=7.5 Hz);
2.66 (d, 1H, J=11 Hz);
3.56 (dd, 1H, J=11+5 Hz);
4.20 (d, 1H, J=9 Hz);
4.53 (m, 1H);
5.67 (s, 1H);
6.08 (q, 1H);
7.15–8.25 (m, 7H).

What is claimed is:

1. A (3aS–6aR)-tetrahydrofuroimidazole derivative of formula:

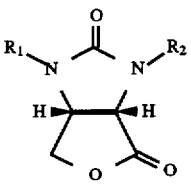

wherein R$_1$ is an (R)- or (S)-1-phenylethyl, whose aromatic nucleus is substituted with one or more substituents with one or more substituents selected from the group consisting of (C$_1$–C$_6$)-alkyl, (C$_1$–C$_6$)-alkoxy, hydroxy, halo, amino, (C$_1$–C$_6$)-alkylamino and (C$_1$–C$_6$)-dialkylamino, or an (R)- or (S)-1-naphthylethyl, whose aromatic nuclei are optionally substituted with one or more substituents selected from the group consisting of (C$_1$–C$_6$)-alkyl, (C$_1$–C$_6$)-alkoxy, hydroxy, halo, amino, (C$_1$–C$_6$)-alkylamino and (C$_1$–C$_6$)-dialkylamino, and R$_2$ is hydrogen or a protective group, which is cleavable in a known manner.

* * * * *